United States Patent [19]

Cheng

[11] Patent Number: 4,832,194

[45] Date of Patent: May 23, 1989

[54] TOOTHPICK DISPENSER

[76] Inventor: Peter S. C. Cheng, 5 Ross Street, Toronto, Ontario, Canada, M5T 1Z8

[21] Appl. No.: 261,076

[22] Filed: Oct. 24, 1988

[51] Int. Cl.⁴ .............................................. B65D 85/28
[52] U.S. Cl. ................................... 206/380; 206/443; 206/620
[58] Field of Search .............. 206/372, 443, 620, 601, 206/634, 380

[56] References Cited

U.S. PATENT DOCUMENTS

| | | | |
|---|---|---|---|
| 2,479,739 | 8/1949 | Gorman, Jr. | 206/372 |
| 2,545,611 | 3/1951 | Flannery | 206/380 |
| 3,331,499 | 7/1967 | Jost | 206/380 |
| 3,768,635 | 10/1973 | Eggert | 206/380 |
| 4,189,048 | 2/1980 | Gaillard | 206/372 |
| 4,637,512 | 1/1987 | Smith | 206/380 |

*Primary Examiner*—Joseph Man-Fu Moy
*Attorney, Agent, or Firm*—Kirschstein, Ottinger, Israel & Schiffmiller

[57] ABSTRACT

A flat toothpick dispenser supports toothpicks in a common plane with a carrier. Each toothpick is supported by webs integral with the carrier. A border surrounds the toothpicks and prevents pointed end portions thereof from becoming exposed during use. Spacer portions integral with the carrier enable toothpicks to be detached one at a time.

10 Claims, 1 Drawing Sheet

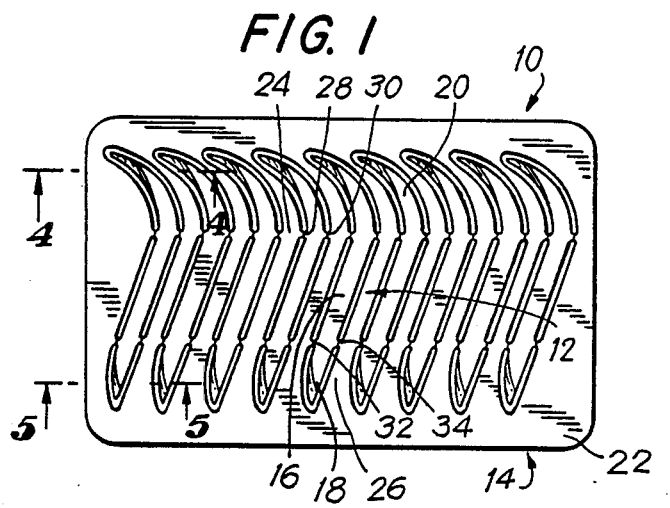
FIG. 1
FIG. 2
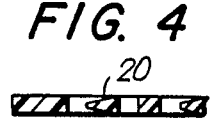
FIG. 4
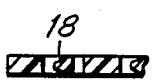
FIG. 5
FIG. 3

TOOTHPICK DISPENSER

BACKGROUND OF THE INVENTION

1. Field of the Invention

This invention generally relates to a toothpick dispenser and, more particularly, to a pocket-sized package for hygienically dispensing toothpicks.

2. Description of Related Art

Packages for dispensing toothpicks are known. U.S. Pat. No. 1,462,062 discloses a card having score lines converging inwardly from the margin of the card to form the outlined edges of toothpicks to be separated from the card by bending the card along the score lines. U.S. Pat. No. 281,731 discloses wooden toothpicks glued on a flexible fabric with cement, and removable therefrom by breaking the cemented bond. U.S. Pat. No. 3,913,596 discloses triangular toothpicks defined by pre-weakened or partially pre-cut tear lines formed edgewise on a ribbon. U.S. Pat. No. 1,382,459; 2,762,501 and 3,438,486 disclose toothpicks having pointed ends received in matchbook style booklets. U.S. Pat. No. 298,502 discloses match splints glued to a paper backing. U.S. Pat. No. 2,192,733 relates to a packet of manicure devices mounted in a matchbook style booklet.

Experience has shown that the known toothpick dispenser packages have not proven to be altogether satisfactory in use. Bending along a score line located between adjacent toothpicks interconnected in edgewise manner does not always produce a clean edge for the separated toothpick. In many cases, it is difficult to detach only a single toothpick from its carrier without inadvertently detaching an adjacent toothpick. Often, to gain leverage, a user must place his or her finger over the pointed end of a toothpick to detach the same, in which event, the user's fingers soil the toothpick end which is to be subsequently inserted in one's mouth to dislodge food and other debris caught between the teeth.

It is often desirable to carry the toothpick dispenser on one's person, for example, in one's pocket. In many dispensers, once one or more toothpicks are detached from their common carrier, sharp edges become exposed, and such exposed edges can punch holes in one's pockets and, in certain cases, may even injure the user, thereby representing a safety hazard.

SUMMARY OF THE INVENTION

1. Objects of the Invention

It is a general object of this invention to overcome the aforementioned drawbacks of known toothpick dispensers.

It is another object of this invention to provide a compact pocket-sized toothpick dispenser which does not expose sharp edges during use.

A further object of this invention is to hygienically dispense toothpicks.

Still another object of this invention is to readily detach toothpicks, one at a time, without requiring excessive strength.

Yet another object of this invention is to avoid forming rough jagged edges on the toothpick during its detachment.

2. Features of the Invention

In keeping with these objects, and others which will become apparent hereinafter, one feature of this invention resides, briefly stated, in a toothpick dispenser comprising a plurality of generally planar toothpicks lying in a common plane, and a generally planar carrier for supporting the toothpicks in a mutually spaced-apart relationship, preferably one after another, along a row in said common plane.

Each toothpick has an elongated handle portion and at least one pointed end portion. Preferably, each toothpick has to pointed end portions, all of the toothpicks being arranged in a nested relationship.

The carrier includes a frame portion which extends peripherally about the toothpicks and past the respective pointed end portions thereof. The frame portion ensures that no sharp edges will be exposed at the periphery of the carrier at any time during dispensing, thus promoting the safe use of the dispenser and avoiding the prior art safety hazard inherent in exposing sharp edges to be carried about on one's person.

The carrier further includes a plurality of spacer portions integral with the frame portion. Preferably, each spacer portion is located between two adjacent toothpicks along the row. The spacer portions serve to reliably enable the user to separate only one toothpick at a time, since adjacent toothpicks are not directly connected to each other in an edgewise manner.

The carrier further includes breakable attachment portions, e.g. webs, integral with the carrier and attached to the respective handle portion of each toothpick. The webs are operative for detachably holding each toothpick at a spacing from the carrier in said common plane. Advantageously, the webs extend from a respective spacer portion across said spacing to opposite longitudinal edges of a respective handle portion of an adjacent toothpick. The webs are arranged in pairs, the pairs being spaced apart along the elongation of a respective handle portion. Each toothpick is held only by the webs which constitute the sole means for supporting the toothpicks on the carrier. Hence, each toothpick is already pre-cut and is, in fact, spaced away from the carrier at all places except at the webs. This enables each toothpick not only to be easily detached, but also to have a clean, non-jagged edge at each of its pointed end portions.

Finally, each planar toothpick has opposite flat surfaces of relatively broad expanse, at least when compared to conventional toothpicks having a circular cross-section. These broad expanses allow advertising indicia to be applied to each toothpick.

The novel features which are considered as characteristic of the invention are set forth in particular in the appended claims. The invention itself, however, both as to its construction and its method of operation, together with additional objects and advantages thereof, best will be understood from the following description of specific embodiments when read in connection with the accompanying drawings.

BRIEF DESCRIPTION OF THE DRAWINGS

FIG. 1 is a front view of a toothpick dispenser according to this invention;

FIG. 2 is a top plan view of the dispenser of FIG. 1;

FIG. 3 is a side view of the dispenser of FIG. 1;

FIG. 4 is a partly broken-away, enlarged, sectional view taken on line 4—4 looking in the direction of the arrows in FIG. 1; and FIG. 5 is a partly broken-away, enlarged, sectional view taken on line 5—5 looking in the direction of the arrows in FIG. 1.

DETAILED DESCRIPTION OF THE PREFERRED EMBODIMENT

Referring now to the drawings, reference numeral 10 generally identifies a toothpick dispenser comprising a plurality of generally planar toothpicks 12 supported in a generally planar carrier 14. As shown in FIGS. 2 and 3, the toothpicks lie in the same plane as the carrier. Each toothpick has an elongated handle or central portion 16, and first and second pointed end portions 18, 20 at opposite ends of the handle portion. The toothpicks are arranged one after another along a row. As shown, nine toothpicks are spaced apart from one another, although it will be understood that more or fewer than that number may be supported on the carrier. Each toothpick has flat major surfaces on opposite sides thereof which enable advertising indicia to be affixed, e.g. by printing, thereon.

The carrier 14 includes a frame portion or border 22 which extends peripherally about the toothpicks and past the respective pointed end portions 18, 20 thereof. Advantageously, the border has a generally rectangular shape with rounded corners. As shown in FIG. 1, the carrier has the general shape and size of a conventional credit card so that it can easily be fitted in one's pocket, purse or wallet.

The carrier 14 further includes a plurality of spacer portions, e.g. 24, 26, at opposite sides of representative toothpick 12. The spacer portions are integral with the border 22. Each spacer portion is located between two adjacent toothpicks along the row. The spacer portions are operative to space the toothpicks apart from one another in a non-touching nested relationship. Put another way, adjacent toothpicks are not directly connected to each other along their longitudinal edges.

The carrier 14 still further includes breakable attachment portions or webs, e.g. 28, 30; and 32,34. The webs are integral with the carrier, and are operative for detachably holding each toothpick at a spacing from the carrier in said common plane.

As best shown in FIG. 1, webs 28,30 extend from spacer portions 24,26 across said spacing to opposite longitudinal edges of a respective handle portion 16 of representative toothpick 12 at a location adjacent pointed end portion 20. Similarly, webs 32,34 extend from spacer portions 24,26 across said spacing to opposite longitudinal edges of the handle portion 16 of toothpick 12 at another location adjacent pointed end portion 18. The pair of webs 28,30 is spaced apart from the pair of webs 32,34 in a direction along the elongation of the handle portion 16.

The webs constitute the sole means for supporting each toothpick on the carrier. As illustrated, only four such webs are utilized to support toothpick 12. However, it will be readily understood by those skilled in the art that more or fewer than four webs can be so utilized.

As clearly shown in FIG. 1, each toothpick is held at a distance from the carrier and is only supported thereon at the webs. Each pointed end portion 18, 20 is pre-cut and, after detachment, has a clean non-jagged peripheral edge.

In the preferred embodiment, the pointed end portion 20 has an arcuate shape, while the pointed end portion 18 extends generally along the elongation of the handle portion 16.

Alternatively, only two webs, each positioned at different locations along each handle portion, can be used to support a respective toothpick. For example, only webs 28, 34 or webs 30, 32 can be employed.

During the dispensing of each toothpick, and even after all the toothpicks have been dispensed, the frame portion retains its generally rectangular shape, thereby not presenting any exposed sharp edges or points which might tend to injure the user.

It will be understood that each of the elements described above, or two or more together, also may find a useful application in other types of constructions differing from the types described above.

While the invention has been illustrated and described as embodied in a toothpick dispenser, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

I claim:

1. A toothpick dispenser, comprising:
   (A) a plurality of generally planar toothpicks lying in a common plane, each toothpick having an elongated handle portion and at least one pointed end portion; and
   (B) a generally planar carrier for supporting the toothpicks in a mutually spaced-apart relationship in said common plane, said carrier including
      (i) a frame portion extending peripherally about the toothpicks and past the respective pointed end portions thereof,
      (ii) a plurality of spacer portions integral with the frame portion, each spacer portion being located between adjacent toothpicks, and
      (iii) breakable attachment portions integral with the carrier and attached to each toothpick, and operative for detachably holding each toothpick at a spacing from the carrier in said common plane to facilitate hygienic detachment of each toothpick from the carrier.

2. The dispenser as recited in claim 1, wherein each toothpick has two pointed end portions, at least one of which has an arcuate shape.

3. The dispenser as recited in claim 1, wherein the frame portion has a generally rectangular shape with rounded corners, said shape being retained during and after dispensing of the toothpicks.

4. The dispenser as recited in claim 1, wherein the carrier supports the toothpicks, one after another, along a row, each spacer portion being located between two adjacent toothpicks along the row.

5. The dispenser as recited in claim 1, wherein the handle portion of each toothpick has opposite longitudinal edges, and wherein at least some of the attachment portions extend from a respective spacer portion across said spacing to the longitudinal edges of the respective handle portion of an adjacent toothpick.

6. The dispenser as recited in claim 5, wherein the attachment portions include at least one pair of webs.

7. The dispenser as recited in claim 6, wherein the webs constitute the sole means for supporting the toothpicks on the carrier.

8. The dispenser as recited in claim 1, wherein each toothpick has opposite flat surfaces for bearing advertising indicia.

9. A toothpick dispenser, comprising:
(A) a plurality of generally planar toothpicks lying in a common plane, each toothpick having an elongated handle portion and at least one pointed end portion; and
(B) a generally planar carrier for supporting the toothpicks in a mutually spaced-apart relationship, one after another, along a row in said common plane, said carrier including
  (i) a frame portion extending peripherally about the toothpicks and past the respective pointed end portions thereof,
  (ii) a plurality of spacer portions integral with the frame portion, each spacer portion being located between two adjacent toothpicks along the row, and
  (iii) breakable attachment portions integral with the carrier and attached to the respecgive handle portion of each toothpick, and operative for detachably holding each toothpick at a spacing from the carrier in said common plane to facilitate hygienic detachment of each toothpick from the carrier.

10. A toothpick dispenser, comprising:
(A) a plurality of generally planar toothpicks lying in a common plane, each toothpick having an elongated handle portion and at least one pointed end portion; and
(B) a generally planar, credit card-sized carrier for supporting the toothpicks in a mutually spaced-apart relationship, one after another, along a row in said common plane, said carrier including
  (i) a generally rectangular frame portion extending peripherally about the toothpicks and past the respective pointed end portions thereof,
  (ii) a plurality of spacer portions integral with the frame portion, each spacer portion being located between two adjacent toothpicks along the row, and
  (iii) breakable attachment portions integral with the carrier and attached solely to the respective handle portion of each toothpick at spaced-apart zones arranged along the elongation of the respective handle portion, said attachment portions being operative for detachably holding each toothpick at a spacing from the carrier in said common plane, the pointed end portion of each toothpick being held at a spacing away from the carrier in said common plane to facilitate hygienic detachment of each toothpick from the carrier.

* * * * *